US006797697B2

(12) United States Patent
Seiberg et al.

(10) Patent No.: US 6,797,697 B2
(45) Date of Patent: Sep. 28, 2004

(54) COMPOSITION CONTAINING A PEPTIDE AND A PIGMENT AND THE USE THEREOF IN DARKENING THE SKIN

(75) Inventors: Miri Seiberg, Princeton, NJ (US); Stanley S. Shapiro, Livingston, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/861,972

(22) Filed: May 21, 2001

(65) Prior Publication Data

US 2002/0197219 A1 Dec. 26, 2002

(51) Int. Cl.$^7$ .................... A61K 38/08; A61K 7/021; A61K 7/42
(52) U.S. Cl. ........................... 514/17; 424/63
(58) Field of Search ............... 424/63; 514/17

(56) References Cited

U.S. PATENT DOCUMENTS

| | | |
|---|---|---|
| 3,755,560 A | 8/1973 | Dickert et al. |
| 4,254,105 A | 3/1981 | Fukuda |
| 4,421,769 A | 12/1983 | Dixon et al. |
| 4,453,941 A | 6/1984 | Jacobs |
| 4,960,764 A | 10/1990 | Figueroa, Jr. et al. |
| 5,216,116 A | 6/1993 | Pawelek |
| 5,218,079 A | 6/1993 | Pawelek et al. |
| 5,225,435 A | 7/1993 | Pawelek et al. |
| 5,227,459 A | 7/1993 | Pawelek et al. |
| 5,260,065 A | 11/1993 | Mathur et al. |
| 5,384,116 A | 1/1995 | Pawelek et al. |
| 5,618,519 A | 4/1997 | Pawelek et al. |
| 5,698,184 A | 12/1997 | Pickart |
| 5,744,125 A | 4/1998 | Pawelek et al. |
| 5,763,575 A | 6/1998 | Sundelin et al. |

FOREIGN PATENT DOCUMENTS

| | | | |
|---|---|---|---|
| EP | 0 273 202 B1 | 6/1995 | |
| FR | 2691465 A | 11/1993 | |
| JP | 2000136124 A * | 5/2000 | ............ A61K/7/48 |
| WO | WO 96/31194 A2 | 4/1996 | |
| WO | WO 99/37279 A1 | 11/1998 | |
| WO | WO 00/15188 A1 | 3/2000 | |
| WO | WO 00/62743 A2 | 10/2000 | |

OTHER PUBLICATIONS

Feit et al., "Inherency in Patent Law" (Jan., 2003) J. Pat. Trademark Off. Soc., 85(1), 5–21.*
U.S. patent application Ser. No. 09/862,145, Johnson & Johnson Consumer Companies, Inc., pending.
U.S. patent application Ser. No. 09/861,973, Johnson & Johnson Consumer Companies, Inc., pending.
John A. Wenninger, G.N. McEwen, Jr.,International Cosmetic Ingredient Dictionary and Handbook, (1997), 1612–1613, 1626, 1654–1661, 1673–1686, 1693–1697,Seventh Edition 1997, vol. 2, The Cosmetic, Toiletry, and Fragrance Association, Washington, DC.

Miklos Bodanszky, In Search of new methods in peptide synthesis, (1985) 449–747, International J. Peptide Protein Research 25, Munksgaard International Pubblishers Ltd. Copenhagen Denmark.
Michael Mezei, Vijeyalakshmi Gulasekharam, Liposomes–A selective drug delivery system for the topical route of adminstration: gel dosage form, (1982) Journal Pharm. Pharacol. 34:473–474.
Susan M. Niemiec, Chandrasekharan Ramachandran, Norman Weiner, Influence of Nonionic Liposomal Composition on Topical Delivery of Peptide Drugs into Pilosebaceous Units: An in Vivo Study Using the Hamster Ear Model, (1995), Pharmaceutical Research, vol. 12, No. 8:1184–1188, Plenum Publishing Corporation.
Petra Boukamp, Rule T. Petrussevska, Dirk Breitkreutz, Jurgen Hornung, Alex Markham, Norbert E. Fusenig, Normal Keratinization in a Spontaneously Immortalized Aneuploid Human Keratinocyte Cell Line, (1988), The Journal of Cell Biology, vol. 106:761–771, The Rockefeller University Press.
M. Seiberg, C. Paine, E. Sharlow, P. Andrade–Gordon, M. Costanzo, M. Eisingr, S. S. Shapiro, The Protease–Activated Receptor 2 Regulates Pigmentation via Keratinocyte–Melanocyte Interactions, (2000), Experimental Cell Research, 25–32, Academic Press.
E.R. Sharlow, C.S. Paine, L. Babiarz, M. Eisinger, S. Shapiro, M. Seiberg, The protease–activated receptor–2 upregulates keratinocyte phagocytosis, (2000)Journal of Cell Science 113:3093–3101, The Company of Biologists Limited.
Miri Seiberg, Christine Paine, Elizabeth Sharlow, Patricia Andrade–Gordon, Michael Constanzo, Magdalena Eisinger and Stanley S. Shapiro, Inhibition of Melanosome Transfer Results in Skin Lightening, (2000), The Journal of Investigative Dermatology, vol. 115, No.2:162–167, The Society of Investigative Dermatology, Inc.
Dezna C. Sheehan, Barbara B. Hrapchak, Theory and practice of Histotechnology, (1980), 223,224,277 Second Edition, Battle Press.
D.D. Breimer, P. Speiser, Liposomes as a Skin Drug Delivery System, Topics in Pharmaceutical Sciences (1985), Elsevier Science Publishers, New York, pp. 345–358.
McCutcheon's Emulsifiers & Detergents, 1986 North American Edition, pp. 317–324.
Cosmetics Science and Technology, 1972 John Wiley & Sons, Inc. Canada, pp. 32–43, 72–73, 443–465.
U.S. patent application Ser. No. 2002/197219, Seiberg et al., filed Dec. 26, 2002.
Chemical Abstracts, vol. 127, No. 16, 1997 Columbus, Ohio, US, abstract No. 218497e. S. Tajima et al: "Modulation by elastin peptide VGVAPG of cell proliferation and elastin expression in human skin fibroblasts"XP002231281 & Arch, Dermatol Res., vol. 289, No. 8, 1997 pp. 489–492.
PCT Search Report for PCT/US 02/16709 dated Feb. 14, 2003.

* cited by examiner

Primary Examiner—Jon P. Weber
(74) Attorney, Agent, or Firm—William E. McGowan

(57) ABSTRACT

The present invention relates to compositions containing a peptide(s) and a pigment(s) and the use of such peptides or such compositions in darkening the skin.

4 Claims, No Drawings

COMPOSITION CONTAINING A PEPTIDE AND A PIGMENT AND THE USE THEREOF IN DARKENING THE SKIN

BACKGROUND OF THE INVENTION

The darkening of skin color is a concern for many individuals. Most people obtain darker skin through exposure to UV light (e.g., suntanning or UV lamps). UV exposure, however, results in accelerated skin aging and increased incidence of skin cancer. The ability to generate a tanned appearance without incurring photodamage, thus, is important to many individuals. Accordingly, alternative methods for "sunless tanning" have evolved.

One method is the use of products containing dihydroxy acetone (DHA). Some of these products, however, produce color that is too orange and unnatural to the user. Moreover, the DHA-produced skin color only minimally protects the user from UV irradiation. Products containing beta-carotene and cantaxanthin have also been used to darken the skin. These products, however, also result in unnatural skin color and reduced sun-protection as compared to naturally tanned skin. Thus, a product is desired that could enhance the body's natural pigment content, resulting in a desired skin color and enhanced photo-protection, without the need of UV exposure.

SUMMARY OF THE INVENTION

The present invention relates to compositions containing a peptide(s) and a pigment(s) and the use thereof in darkening the skin.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Definitions

What is meant by "darkening the skin" is darkening the appearance of the skin, including, but not limited to, tanning the skin.

As used herein, "topical applying" means directly laying on or spreading on outer skin using, e.g., by use of the hands or an applicator such as a wipe, roller, or spray.

As used herein, "cosmetically-acceptable" means that the peptides, pigments, or inert ingredients which the term describes are suitable for use in contact with tissues (e.g., the skin) without undue toxicity, incompatibility, instability, irritation, allergic response, and the like.

As used herein, "safe and effective amount" means an amount of the peptide or composition sufficient to induce a darkening of the skin, but low enough to avoid serious side effects. The safe and effective amount of the compound or composition will vary with the area being treated, the age and skin type of the end user, the duration and nature of the treatment, the specific compound or composition employed, the particular cosmetically-acceptable carrier utilized, and like factors.

Pigment

What is meant by a "pigment" is a compound(s) that can be taken up by epidermal cells in the presence of the peptides described below, resulting in visually darker look to the skin. Examples of such pigments include, but not limiting to, melanin and melanin derivatives (e.g, both melanin polymers and lower molecular weight water-soluble melanin derivatives); extracts from natural sources containing pigments (e.g., brown pigments from plants from the Hedychium genus or Bearberry genus or yellow, orange and red pigments, from plants containing carotenoids or canthaxanthins); or synthetic chemicals such as compounds containing copper (e.g., copper salts such as $CuCl_2$) or synthetic carotenoids or canthaxantins. What is meant by an "extract" is a mixture of compounds isolated from a natural source (e.g., a plant). Examples of synthetic melanin derivatives are disclosed in U.S. Pat. Nos. 5,618,519, 5,384,116, and 5,227,459. Examples of soluble melanin derivatives are disclosed in U.S. Pat. Nos. 5,744,125, 5,225,435, 5,218,079, and 5,216,116. Examples of commercially available soluble melanin derivatives include Melasyn-100™ from San-mar laboratories, Inc. (Elmsford, N.Y.) and MelanZe™ from Zylepsis (Ashford, Kent, United Kingdom).

The amount of pigment present in the composition will depend on the type of pigment used. The pigment typically will be present in the composition in an amount from about 0.001% to about 20% by weight, in particular in an amount from about 0.005% to about 5% by weight.

Peptides

The composition of the present invention comprises a peptide of the formula I $$R_1 \\ >Val-Gly-Val-Ala-Pro-Gly-R_3 \quad \text{Formula I} \\ R_2$$

wherein:

each $R_1$ and $R_2$, independently, is H, $C_{1-12}$ alkyl, $C_{7-10}$ phenylalkyl, or $C(=O)E_1$, where $E_1$ is $C_{1-20}$ alkyl, $C_{3-20}$ alkenyl, $C_{3-20}$ alkynyl, phenyl, 3,4-dihydroxyphenylalkyl, naphthyl, or $C_{7-10}$ phenylalkyl; provided that when either $R_1$ or $R_2$ is $C(=O)E_1$, the other must be H; and $R_3$ is OH, $NH_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino;

or a cosmetically acceptable salt thereof;

In one embodiment, $R_1$ and $R_2$, which are bound to the N-terminus of the peptide, are both H. In another embodiment, $R_1$ is H and $R_2$ is $C(=O)E_1$ (e.g., palmitoyl, oleatoyl, or stearatoyl).

Examples of peptides of the present invention include, but are not limited to, $H_2$—Val—Gly—Val—Ala—Pro—Gly—$NH_2$ (Peptide 1, SEQ ID NO:1), $H_2$—Val—Gly—Val—Ala—Pro—Gly—OH (SEQ ID NO:2), Palmitoyl—Val—Gly—Val—Ala—Pro—Gly—$NH_2$ (Peptide 1, SEQ ID NO:3), Palmitoyl—Val—Gly—Val—Ala—Pro—Gly—OH (SEQ ID NO:4), Stearatoyl—Val—Gly—Val—Ala—Pro—Gly—$NH_2$ (SEQ ID NO:5), and Stearatoyl—Val—Gly—Val—Ala—Pro—Gly—OH (SEQ ID NO:6), or a cosmetically-acceptable salt thereof.

The symbol $A_1$, $A_2$, or the like used herein (e.g., in Figure 1) stands for the residue of an alpha-amino acid. Such symbols represent the general structure, —NH—CH(X)—CO— or =N—CH(X)—CO— when it is at the N-terminus or —NH—CH(X)—CO— when it is not at the N-terminus, where X denotes the side chain (or identifying group) of the alpha-amino acid, e.g., X is —CH(CH$_3$)$_2$ for Val. Note that the N-terminus is at the left and the C-terminus at the right in accordance with the conventional representation of a polypeptide chain. R$_1$ and R$_2$ are both bound to the free nitrogen atom N-terminal amino acid (e.g., Val) and the R$_3$ is bound to the free carboxy group of the C-terminal amino acid (e.g., Gly).

Furthermore, where the amino acid residue is optically active, it is the L-form configuration that is intended unless the D-form is expressly designated. An alkyl group, if not specified, contains 1–12 carbon atoms.

The peptide of the invention can be provided in the form of cosmetically acceptable salts. Examples of preferred salts are those with therapeutically acceptable organic acids, e.g., acetic, palmitic, oleic, stearic, lactic, maleic, citric, malic, ascorbic, succinic, benzoic, salicylic, methanesulfonic, or pamoic acid, as well as polymeric acids such as tannic acid or carboxymethyl cellulose, and salts with inorganic acids such as the hydrohalic acids (e.g., hydrochloric acid), sulfuric acid or phosphoric acid.

The amount of peptide present in the composition will depend on the peptide used. The peptide typically will be present in the composition in an amount from about 0.001% to about 10% by weight, in particular in an amount from about 0.005% to about 5% by weight.

The method for synthesizing peptides of the present invention are well documented and are within the ability of a person of ordinary skill in the art. See, e.g., Bodanszky M, Int J Pept Protein Res 25(5):449–74 (1985), Fmoc Solid Phase Peptide Synthesis, eds. Chan, W. & White, P. (Oxford University Press, 2000), and Chemial Approaches to the Synthesis of Peptides and Proteins, Lloyd-Williams, P. et al. (CRC Press, 1997).

Topical Compositions

The topical compositions useful in the present invention involve formulations suitable for topical application to skin. In one embodiment, the composition comprises the peptide, pigment, and a cosmetically-acceptable topical carrier. In one embodiment, the cosmetically-acceptable topical carrier is from about 50% to about 99.99%, by weight, of the composition (e.g., from about 80% to about 95%, by weight, of the composition.

The compositions may be made into a wide variety of product types that include but are not limited to lotions, creams, gels, sticks, sprays, ointments, cleansing liquid washes and solid bars, shampoos, pastes, foams, powders, mousses, shaving creams, wipes, patches, nail lacquers, wound dressing and adhesive bandages, hydrogels, films and make-up such as foundations, mascaras, and lipsticks. These product types may comprise several types of cosmetically-acceptable topical carriers including, but not limited to solutions, emulsions (e.g., microemulsions and nanoemulsions), gels, solids and liposomes. The following are non-limitative examples of such carriers. Other carriers can be formulated by those of ordinary skill in the art.

The topical compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, and mixtures thereof.

Topical compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972) and the International Cosmetic Ingredient Dictionary and Handbook, eds. Wenninger and McEwen, pp. 1656–61, 1626, and 1654–55 (The Cosmetic, Toiletry, and Fragrance Assoc., Washington, D.C., 7$^{th}$ Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72–73 (1972) and the ICI Handbook pp. 1693–1697.

The topical compositions useful in the present invention formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, U.S. Pat. Nos. 3,755,560, 4,421,769, McCutcheon's Detergents and Emulsifiers, North American Edition, pp. 317–324 (1986), and the ICI Handbook, pp.1673–1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. Nos. 4,254,105 and 4,960,764, are also useful in the subject invention. In general, such single or multiphase emulsions contain water, emollients, and emulsifiers as essential ingredients.

The topical compositions of this invention can also be formulated as a gel (e.g., an aqueous, alcohol, alcohol/water, or oil gel using a suitable gelling agent(s)). Suitable gelling agents for aqueousand/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The topical compositions of the present invention can also be formulated into a solid formulation (e.g., a wax-based stick, soap bar composition, powder, or a wipe containing powder).

Liposomal formulations are also useful compositions of the subject invention. In one embodiment, the peptide and/or the pigment are contained within the liposome. Examples of liposomes are unilamellar, multilamellar, and paucilamellar liposomes, which may or may not contain phospholipids. Such compositions can be prepared by first combining hesperetin with a phospholipid, such as dipalmitoylphosphatidyl choline, cholesterol and water according to the method described in Mezei & Gulasekharam, "Liposomes—A Selective Drug Delivery System for the Topical Route of Administration; Gel Dosage Form", Journal of Pharmaceutics and Pharmacology, Vol. 34 (1982), pp. 473–474, or a modification thereof. Epidermal lipids of suitable composition for forming liposomes may be substituted for the phospholipid. The liposome preparation may then incorporated into one of the above carriers (e.g., a gel or an oil-in-water emulsion) in order to produce the liposomal formulation. Other compositions and uses of topically applied liposomes are described in Mezei, M., "Liposomes as a Skin Drug Delivery System", Topics in Pharmaceutical Sciences (D. Breimer and P. Speiser, eds.), Elsevier Science Publishers B. V., New York, N.Y., 1985, pp. 345–358, PCT Patent Application No. WO96/31194, Niemiec, et al., 12 Pharm. Res. 1184–88 (1995), and U.S. Pat. No. 5,260,065.

In one-embodiment, the liposome is non-ionic. In one example, the liposome contains (a) glycerol dilaurate; (b) compounds having the steroid backbone found in cholesterol; and (c) fatty acid ethers having from about 12 to about 18 carbon atoms. In a further embodiment, the liposome comprises glycerol dilaurate, cholesterol, polyoxyethylene-10-stearyl ether, and polyoxyethylene-9-lauryl ether. In one embodiment, these ingredients are in a ratio of about 38:12:33:17.

In one embodiment, the liposomes are present in the topical composition in an amount, based upon the total volume of the composition, of from about 10 mg/ml to about 100 mg/ml such as from about 15 mg/ml to about 50 mg/ml. Methods of preparing liposomes are well known in the art, such as those disclosed in The topical compositions useful in the subject invention may contain, in addition to the aforementioned components, a wide variety of additional oil-soluble materials and/or water-soluble materials conventionally used in compositions for use on skin, hair, and nails at their art-established levels.

Additional Cosmetically Active Agents

In one embodiment, the topical composition further comprises another cosmetically active agent in addition to the peptides and pigments. What is meant by a "cosmetically active agent" is a compound (e.g., a synthetic compound or a compound isolated from a natural source) that has a cosmetic or therapeutic effect on the skin, hair, or nails, including, but not limiting to e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly—His—Lys, coenzyme Q10, peptides such as those disclosed in PCT Patent Application WO00/15188, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera and legumes such as soy beans, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited to, glycolic acid, lactic acid, malic acid, salicylic acid, citric acid, and tartaric acid. See, e.g., European Patent Application No. 273,202.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinal and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612–13 of the ICI Handbook.

Other Materials

Various other materials may also be present in the compositions useful in the subject invention. These include humectants, proteins and polypeptides, preservatives and an alkaline agent. Examples of such agents are disclosed in the ICI Handbook, pp.1650–1667. The compositions of the present invention may also comprise chelating agents (e.g., EDTA) and preservatives (e.g., parabens). Examples of suitable preservatives and chelating agents are listed in pp. 1626 and 1654–55 of the ICI Handbook. In addition, the topical compositions useful herein can contain conventional cosmetic adjuvants, such as dyes, opacifiers (e.g., titanium dioxide), pigments, and fragrances.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water comprises at least about 10 mg/L of calcium and/or at least about 5 mg/L of magnesium.

The composition and formulations containing such compositions of the present invention may be prepared using methodology that is well known by an artisan of ordinary skill.

EXAMPLE 1

Induced Pigmentation in Culture

The peptide Peptide 1 and various pigments were tested, alone or in combination, with keratinocyte-melanocyte cultures for their effect on cell pigmentation, using DOPA staining and computerized image analysis. The pigments that were tested were copper chloride from Sigma (St. Louis, Mo.) and the water-soluble melanin derivative Melasyn-100™ from San-mar laboratories, Inc. (Elmsford, N.Y.). The pigments were tested at concentrations ranging from 0.0001% (W/V) to 0.1% (W/V) and peptides were tested at 50 $\mu$M.

The assay was conducted in the following manner. Human HaCaT keratinocytes (Boukamp P., et al., J Cell Biol 106, 3, 761–771 (1988)) were maintained in Dulbecco's Modified Eagle's Medium (DMEM) containing 10% fetal bovine serum (FBS), 4.5 mg/ml glucose, 2 mM L-glutamine, 50 U/ml penicillin and 50 $\mu$g/ml streptomycin (Life Technologies, Gaithersburg, Md.). Cells were maintained at <80% confluency in 5% $CO_2$ (v/v) and were used in experimental procedures up to culture passage 15. Human primary melanocytes (Clonetics, San Diego, Calif. or Cascade Biologics, Portland, Oreg.) were maintained according to manufacturer's instructions. To establish keratinocyte-melanocyte co-cultures, $6 \times 10^4$ melanocytes were plated in each well of a 24 well plate and maintained according to manufacturer's instructions.

Melanocytes were rinsed three times with melanocyte growth media without PMA and keratinocytes ($6 \times 10^4$) were plated to establish the co-cultures in this media. Co-cultures were treated for three days with test peptides and pigments, and assayed for cell viability and pigment level on the forth day. Cell viability was assayed using alamarBlue™ (Acumed International, West Lake, Ohio) following manufacturer's instructions. No change in viability was observed following three daily treatments with all tested material. All in vitro experiments were performed in triplicates, and were repeated at least three times.

Following three daily treatments, the co-cultures were briefly fixed (10% buffered formalin from Fisher Scientific, 15 minutes), washed three times with Phosphate-buffered saline (PBS, from Life Technologies) and stained with L-3,4-Dihydroxyphenylalanine (DOPA, from Sigma, St. Louis, Mo.) 0.1% in PBS, for 5 hours at 37° C., followed by two PBS washes and formalin (10%, overnight) fixation. DOPA is a substrate for tyrosinase, therefore an increase in staining represents increased tyrosinase activity and pigment production. DOPA-stained monolayers were used for image analysis. All images were obtained and analyzed with Image Pro Plus 3.0 software (Media Cybernetics, Silver Spring, Md.). Parameters measured were surface area of stained material within melanocyte and keratinocytes and the total surface area of the cells in the culture, and the relative pigmented area was calculated. A value of 100% was assigned to untreated controls, and values of treatment groups were normalized to their relevant controls. In all experiments there was no difference between PBS-treated cells and untreated controls. Data are presented with standard deviation (SigmaPlot® 5.0, SPSS Science, Chicago, Ill.).

Table 1 shows the results of representative co-culture experiments, normalized for their relative controls, demonstrating that the combinations of peptides and pigments of the present invention enhanced pigmentation. This Table demonstrates the specificity of the compositions of this invention in inducing pigmentation (e.g., increasing pigmentation by up to 517%). Forskolin (Sigma, St. Louis, Mo.), a known inducer of pigmentation, served as a positive control and a reference point. Forskolin was administered at 1% (W/V).

TABLE 1

| Compositions | Conc. | Mean area | SD | % increase |
|---|---|---|---|---|
| Control | — | 0.079 | 0.028 | — |
| Peptide 1 | 50 $\mu$M | 0.131 | 0.027 | 66.6 |
| Melasyn-100 ™ | 0.1% (W/V) | 0.153 | 0.033 | 95.0 |
| Peptide 1 + Melasyn-100 ™ | 50 $\mu$M 0.0001% (W/V) | 0.228 | 0.045 | 190 |
| $CuCl_2$ | 0.001% (W/V) | 0.173 | 0.045 | 120 |
| $CuCl_2$ | 0.1% (W/V) | 0.246 | 0.057 | 212 |
| Peptide 1 + $CuCl_2$ | 50 $\mu$M 0.001% (W/V) | 0.189 | 0.033 | 140 |
| Peptide 1 + $CuCl_2$ | 50 $\mu$M 0.1% (W/V) | 0.200 | 0.045 | 155 |

EXAMPLE 2

Induced Pigmentation In Vivo

Compositions of the present invention were tested for their ability to induce in vivo pigmentation in skin cells in the following experiment. Dark skinned Yucatan microswine (Charles River, Portland, Me.) were housed in appropriately sized cages in an environmentally controlled room with a 12-hour light—12-hour dark photoperiod and supplied with food and water ad libitum. Animal care was based on the "Guide for the Care and Use of Laboratory Animals", NIH Publication No. 85–23. Twenty $\mu$l of test peptides were applied topically, twice a day, five days/week, for eight or nine weeks, on the dorsum of the swine. Treatments of individual swine were always arranged in a head to tail order on one side, and in a tail to head order on the other side of the animal. Biopsies were taken using standard techniques. All swine studies presented here had no visual irritation, and histological analyses revealed no markers of irritation or other pathological signs.

Sections from the skin biopsies were stained with Hematoxylin and Eosin (H&E), or with Fontana-Mason (F&M), using standard procedures (Sheenan D C, Hrapckak B B, eds., Theory and Practice of Histo-technology. p. 223, 277, The C. V. Mosby Co., St. Louis (1980)). F&M staining identifies silver nitrate reducing molecules. In skin, this non-specific stain identifies primarily melanin. At least three sections per biopsy were processed. Each experiment was repeated at least three times.

Swine were treated with either: the known skin darkening agent forskolin (Sigma) or with a Coleus forskoli extract (ATZ Naturals, Englewood Cliffs, N.J.) which contains forskolin, as a positive control at 1% (W/V); pigments at 1% or 5% (W/V); peptides of this invention at 250 $\mu$M or 500 $\mu$M; and combinations of such peptides at 250 $\mu$M or 500 $\mu$M with pigments at 1% (W/V). Pigments tested include pigmented natural extracts (i.e., Bearberry extract and Hedychium spicatum extract) and synthetic compounds (i.e., the soluble melanin compound Melasyn-100™). These test compounds were dissolved in ethanol: propylene glycol 70:30 (v/v). In a limited set of experiments, certain peptide and pigment combinations were also tested using different vehicles, in order to possibly enhance delivery, namely liposomes and an aqueous gel system, and the ethanol. Liposomes consisted of glycerol dilaurate/cholesterol/polyoxyethylene-10-stearyl ether/polyoxyethylene-9-lauryl ether at a ratio of 37.5:12.5:33.3:16.7, and were prepared according to Niemiec, et al., 12 Pharm. Res. 1184–88 (1995). The gel delivery system consisted of Sepigel 305 (Polyacrylamide & C13–14 isoparaffin & laureth-7 from SEPPIC, Inc. of Fairfield, N.J.). Sepigel 305 was dissolved in the aqueous formulations at 1–3% (W/V). These delivery systems were also tested in the absence of any pigments or peptides.

Histological analysis revealed an increase in pigment deposition in swine treated with compositions of this invention. This increase was greater than the darkening induced by forskolin or Coleus forskoli extract, which are known skin darkening agents. Occasionally, an individual swine did not respond to any composition or even forskolin (the positive control). Such "non-responder" swine composed less than 25% of the total swine treated.

F&M-stained histological skin sections were evaluated for the change in pigment deposition within the treated site. Criteria for evaluation were total increase in pigment deposition, and the presence of capped epidermal cells above the basal layer. Table 3 represents the average value of all sites of responsive swine treated with each test material. The scale for evaluation is defined in Table 2.

TABLE 2

| Score | Description |
| --- | --- |
| −1 | Slight lightening |
| 0 | No change |
| 1 | Minimal increase in pigment deposition |
| 2 | Increased pigment deposition |
| 3 | Strong increase in pigment deposition, some increase in caps |
| 4 | Strong increase in pigment deposition, strong increase in caps |

TABLE 3

| Compositions | Score |
| --- | --- |
| Control | 0 |
| Forskolin (positive control) | 1 |
| Coleus Forskoli (positive control) | 1 |
| Ethanol: polypropylene glycol | 0 |
| Liposomes | −1 |
| Gel | 0 |
| Peptide 1 | 1 |
| Hedychium Extract | 0 |
| Peptide 1 and Hedychium Extract | 2 |

This example demonstrates that treatments with compositions of peptides and pigments of this invention result in increased pigment production and deposition in vivo.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of darkening the skin, said method comprising topically applying to the skin a safe and effective amount of a composition comprising Palmitoyl-Val—Gly—Val—Ala—Pro—Gly—NH$_2$ or a cosmetically acceptable salt thereof.

2. A method of darkening the skin, said method comprising topically applying to the skin a safe and effective amount of a composition comprising Palmitoyl-Val—Gly—Val—Ala—Pro—Gly—OH or a cosmetically acceptable salt thereof.

3. A method of darkening the skin, said method comprising topically applying to the skin a safe and effective amount of a composition comprising Stearatoyl-Val—Gly—Val—Ala—Pro—Gly—NH$_2$ or a cosmetically acceptable salt thereof.

4. A method of darkening the skin, said method comprising topically applying to the skin a safe and effective amount of a composition comprising Stearatoyl-Val—Gly—Val—Ala—Pro—Gly—OH or a cosmetically acceptable salt thereof.

* * * * *

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide
<221> NAME/KEY: misc_feature
<222> LOCATION: (4)..(4)
<223> OTHER INFORMATION: C-terminal amidation

<400> SEQUENCE: 1

Val Gly Val Ala Pro Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2
```

```
Val Gly Val Ala Pro Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide
<221> NAME/KEY: misc_feature
<222> LOCATION: (1)..(1)
<223> OTHER INFORMATION: Palmitoyl N-terminus
<221> NAME/KEY: misc_feature
<222> LOCATION: (4)..(4)
<223> OTHER INFORMATION: Amidated C-terminus

<400> SEQUENCE: 3

Val Gly Val Ala Pro Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide
<221> NAME/KEY: MISC_FEATURE
<222> LOCATION: (1)..(1)
<223> OTHER INFORMATION: Palmitoyl N-terminus

<400> SEQUENCE: 4

Val Gly Val Ala Pro Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide
<221> NAME/KEY: misc_feature
<222> LOCATION: (1)..(1)
<223> OTHER INFORMATION: Staratoyl N-terminus
<221> NAME/KEY: misc_feature
<222> LOCATION: (1)..(1)
<223> OTHER INFORMATION: Stearatoyl N-terminus
<221> NAME/KEY: misc_feature
<222> LOCATION: (4)..(4)
<223> OTHER INFORMATION: Amidated C-terminus

<400> SEQUENCE: 5

Val Gly Val Ala Pro Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Peptide
<221> NAME/KEY: misc_feature
<222> LOCATION: (1)..(1)
<223> OTHER INFORMATION: Stearatoyl N-terminus

<400> SEQUENCE: 6

Val Gly Val Ala Pro Gly
1               5
```